(12) United States Patent
Damphousse et al.

(10) Patent No.: US 6,261,231 B1
(45) Date of Patent: Jul. 17, 2001

(54) HANDS-FREE ULTRASOUND PROBE HOLDER

(75) Inventors: David J. Damphousse, Brookline, NH (US); Mikhail Kagan, Chelmsford, MA (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/400,383

(22) Filed: Sep. 21, 1999

Related U.S. Application Data (60) Provisional application No. 60/101,337, filed on Sep. 22, 1998.

(51) Int. Cl.⁷ ..................................................... A61B 8/00
(52) U.S. Cl. ............................................ 600/437; 600/459
(58) Field of Search ................................... 600/437, 449, 600/459

(56) References Cited

U.S. PATENT DOCUMENTS

| | | | | |
|---|---|---|---|---|
| 4,316,271 | * | 2/1982 | Evert ..................................... | 600/459 |
| 4,483,344 | * | 11/1984 | Atkov et al. .......................... | 600/459 |
| 4,722,346 | * | 2/1988 | Chen ..................................... | 600/459 |
| 4,796,632 | * | 1/1989 | Boyd et al. ........................... | 600/459 |
| 5,381,794 | * | 1/1995 | Tei et al. .............................. | 600/459 |
| 5,598,845 | * | 2/1997 | Chandraratna et al. ............. | 600/459 |

OTHER PUBLICATIONS

Mercer et al., J. Am. Soc. Of Echocardiography, pp. 363–366 (May 1997).

\* cited by examiner

*Primary Examiner*—Francis J. Jaworski
(74) *Attorney, Agent, or Firm*—Peter L. Dolan (57) ABSTRACT

The present invention relates to an apparatus for holding a probe and a method for using the same. The apparatus comprises a body portion having a longitudinal bore and a membrane holder positioned over a first end of the body portion. The membrane holder defines an opening which is covered by a membrane. A receptacle for receiving the probe is rotatably positioned within the longitudinal bore of the body portion at a second end of the body portion. The membrane, membrane holder, body portion, receptacle, and probe define a sealed chamber for containing a contacting medium.

30 Claims, 5 Drawing Sheets

HANDS-FREE ULTRASOUND PROBE HOLDER

This application claims the benefit of U.S. Provisional Application No. 60/101,337 filed on Sep. 22, 1998.

FIELD OF THE INVENTION

The present invention relates to the field of ultrasound imaging and, more specifically, to an apparatus and a method for holding an ultrasound probe to enable a clinician hands-free imaging capabilities.

BACKGROUND OF THE INVENTION

Ultrasound/contrast imaging is commonly performed by a clinician using a hand held probe which is positioned adjacent to a patient. However, the effective use of a hand held probe is limited by frame-to-frame variability in the images produced, occupational health hazards, and the inability to monitor an organ of interest during exercise induced stress. These limitations can seriously and deleteriously affect the utility of the ultrasound/contrast imaging technique.

Frame-to-frame variability in the images arises from movement of the probe between successive images. To minimize distortions resulting from frame-to-frame variability, the probe must be maintained in a steady orientation relative to the patient. For example, when imaging a patient's heart, 5 to 10 cardiac cycles are typically needed for contrast myocardial perfusion to occur before the next ultrasound wave is emitted. Since a cardiac cycle is typically about 1 second in duration, a clinician must be able to steadily hold a probe for 5 to 10 seconds between successive ultrasonic emissions. Movement of the probe during that time period will result in frame-to-frame variability between images and cardiac views obtained.

Additionally, holding the probe in a steady orientation for long periods of time can lead to occupational health hazards (e.g. ergonomic injuries). Mercer et al., J. Am. Soc. of Echocardiography, pp. 363–366 (May 1997), reported studies relating to the occupational health hazards due to long term use of hand held probes. The hazards include muscle strain and injury from standing over the patient, carpel tunnel syndrome resulting from wrist strain, stress and burnout due to long days of repetitious probe holding, and an increased likelihood of disease transmission between the patient and sonographer.

Further, it is impractical to use a hand held probe to monitor the organ of interest while the patient is undergoing exercise-induced stress. As a result, ultrasound imaging with stress exercise is traditionally performed only before and after the stress is performed. However, it would be beneficial to monitor ultrasound images while the patient is actually undergoing exercise-induced stress.

In light of the foregoing, it would be beneficial to provide an apparatus and a method for hands-free use of an ultrasonic probe to monitor an organ of interest. The apparatus and method should enable the orientation of the probe to be adjusted relative to the patient in order to produce optimal images of the organ of interest. However, once the position of the probe has been adjusted, the apparatus and method should enable the probe to be maintained in that position throughout the ultrasound procedure, in order to minimize the effects of frame-to-frame variability in the images. Further, the apparatus and method should reduce the incidence of occupational health hazards associated with the long term use of hand held probes and enable images of the organ of interest to be produced while the patient is undergoing exercise-induced stress. Additionally, the apparatus and method should be adaptable to work in cooperation with the known hand held ultrasonic probes.

SUMMARY OF THE INVENTION

The problems associated with the use of hand held ultrasonic probes are overcome to a large degree by the present invention. The present invention relates to an apparatus and a method for producing ultrasound images of an object of interest without the need for a clinician to hold and maintain an ultrasonic probe adjacent to the patient near the organ of interest.

The present invention relates to a probe holder for holding a probe comprising a body portion having a longitudinal bore. A membrane holder, defining an opening, is positioned over a first end of the body portion. The size and shape of the membrane holder may be selected to allow for subcostal views or to cover more surface area of the patient without repositioning the probe holder. The membrane holder comprises a longitudinal groove and a ring positioned within the longitudinal groove for holding a membrane to cover the opening. Additionally, a membrane fixture may be positioned within the opening of the membrane holder for securing the membrane to the membrane holder.

A receptacle for receiving the probe is provided. The receptacle has a longitudinal passage and is rotatably positioned within the longitudinal bore of the body portion at or near a second end of the body portion. The membrane, the membrane holder, the body portion, the receptacle, and the probe define a sealed chamber for containing a contacting medium.

In one particular embodiment, the probe holder further comprises an upper membrane, having an opening, positioned over the longitudinal bore of the body portion at the first end of the body portion. A sealing member is provided for securing a perimeter of the opening in the upper membrane to an outer surface of the probe. In this embodiment, the membrane, the membrane holder, the body portion, the upper membrane, and the probe define the sealed chamber for containing the contacting medium.

The receptacle may further comprise a probe securing means positioned within the longitudinal passage of the receptacle for retaining the probe within the receptacle with a window of the probe directed generally toward the opening in the membrane holder. In one embodiment, the probe securing means comprises a rubber tube. Alternatively, the probe securing means comprises a locking cuff, such as an inflatable locking cuff. In yet another embodiment, the probe securing means comprises a multipodal locking devices.

An annular lip may be provided which is formed along an inner surface of the body portion and concentric with the longitudinal bore of the body portion. The annular lip contacts an outer surface of the receptacle and is shaped to provide smooth rotation of the receptacle within the body portion, thereby facilitating manipulation of the probe to obtain optimum ultrasound images of an object of interest.

The probe holder may further comprise a locking means operatively connected to the body portion for maintaining the receptacle in a selected orientation. In one embodiment, the locking means comprises a locking cap positioned over the second end of the body portion, a pressing ring positioned between the locking cap and an outer surface of the receptacle, and an insert positioned between the pressing ring and the outer surface of the receptacle. The locking cap is movable between a first position wherein the receptacle is rotatable within the body portion and a second position wherein the locking cap exerts pressure on the insert through the pressing ring to maintain the receptacle in a selected orientation.

The probe holder is secured to a patient or other subject by a belt, harness, or holster. A coupling means is operatively connected to the belt, harness, or holster for securing the body portion of the probe holder to the belt, harness, or holster with the membrane in contact with the subject.

The present invention also relates to a method for holding a probe adjacent to a subject. The probe is positioned within a probe holder in accordance with the present invention. A contacting medium is then inserted within the sealed chamber of the probe holder. The probe and probe holder are then secured to the subject adjacent to the object of interest. The orientation of the probe is adjusted by rotating the receptacle of the probe holder within the longitudinal channel of the body portion until the resulting ultrasound image of the object of interest is optimized. If desired, the position of the probe is then locked by actuating the locking cap.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
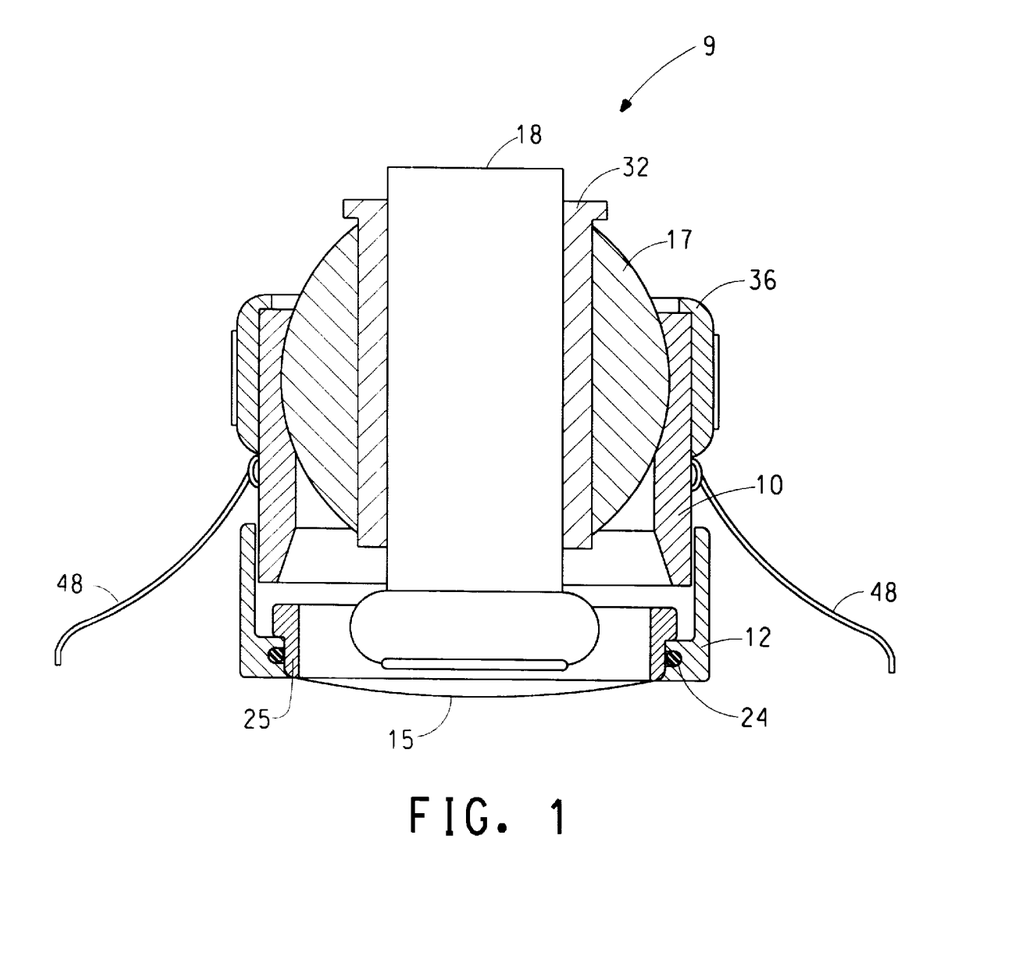
FIG. 1 is a partial cross-sectional view of a probe holder in accordance with the present invention.
Figure 2:
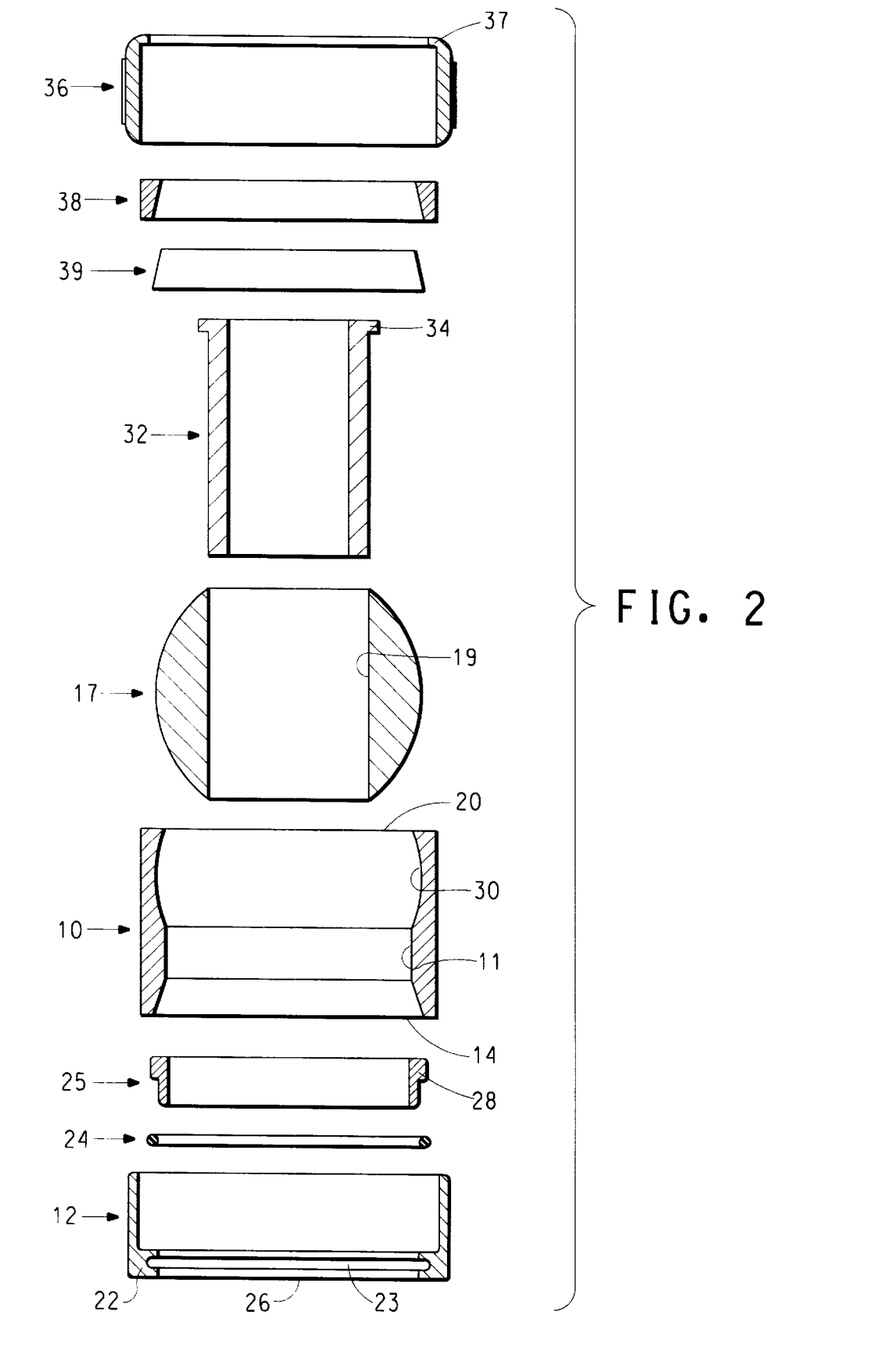
FIG. 2 is an exploded cross-sectional view of the probe holder of FIG. 1.

A probe holder 9 for holding a probe 18 in accordance with the present invention is depicted in FIGS. 1 and 2. The probe holder 9 comprises a generally cylindrical body portion 10 having a longitudinal bore 11 concentric with a longitudinal axis of the body portion 10. A membrane holder 12, defining an opening which is covered by a membrane 15, is positioned over a first end 14 of the body portion 10. A receptacle 17 is provided for receiving the probe 18 within a longitudinal channel or passage 19 of the receptacle 17. The receptacle 17 is rotatably positioned within the longitudinal bore 11 of the body portion 10 at or near a second end 20 of the body portion 10. The membrane 15, the membrane holder 12, the body portion 10, the receptacle 17, and the probe 18 define a sealed chamber for containing a contacting medium.

The membrane holder 12 comprises a generally tubular cap having an inner diameter sized to fit over the first end 14 of the body portion 10. Accordingly, the membrane holder 12 is maintained about the first end 14 of the body portion 10 by friction. Alternatively, the membrane holder 12 may comprise internal threads which mate with external threads along the first end 14 of the body portion 10 for maintaining the membrane holder 12 about the first end 14 of the body portion 10. An annular lip 22, formed along an interior surface of the tubular cap, is provided as a stop surface to maintain the membrane holder 12 in position about the first end 14 of the body portion 10.

The lip 22 also functions to define the opening 26 over which the membrane 15 is stretched. Toward that end, an annular groove 23 is formed about the lip 22 of the membrane holder 12. The groove 23 is designed to accept a resilient O-ring 24. Accordingly, a periphery of the membrane 15 can be secured to the membrane holder 12 by positioning the O-ring 24 within the annular groove 23 so as to maintain the periphery of the membrane 15 within the groove 23.

The probe holder 9 may further comprise a membrane fixture 25 to assist in securing the membrane 15 to the membrane holder 12. The membrane fixture 25 comprises a tubular section that is sized to fit securely within the opening 26 of the membrane holder 12. Accordingly, when the O-ring 24 is positioned within the annular groove 23 of the membrane holder 12 to secure the membrane 15 to the membrane holder 12, the membrane fixture 25 asserts a force against the O-ring 24 thereby strengthening the seal between the membrane 15 and the membrane holder 12. An annular lip 28 is provided along an exterior surface of the membrane fixture 25 as a stop surface to help maintain the membrane fixture 25 in position within the opening 26 of the membrane holder 12.

The membrane 15 is provided to insure that ultrasound signals are transmitted from and received by the probe 18 even as the orientation of the probe 18 is adjusted. Accordingly, the membrane 15 should be manufactured from a material which is capable of conducting ultrasound signals while being flexible enough to conform to the contours of the patient being monitored. For example, the membrane 15 may comprise a section of thin latex, such as that used for surgical gloves.

The receptacle 17 functions to support the probe 18 within the probe holder 9 while enabling the orientation of the probe 18 relative to the patient to be optimized. The receptacle 17 is formed as a sphere having the longitudinal passage 19 formed along a diameter of the sphere. Accordingly, as shown, the receptacle 17 forms a toroid. The diameter of the receptacle 17 is selected so that the receptacle 17 fits within the longitudinal bore 11 of the body portion 10 and is freely rotatable therein. When the probe 18 is inserted within the passage 19 of the receptacle 17, the probe 18 can be manipulated to provide optimal images of the object of interest by rotating the receptacle 17 within the body portion 10. To facilitate rotation of the receptacle 17, an annular lip 30, formed along an inner surface of the body portion 10 and concentric with the longitudinal bore 11 of the body portion 10, is provided for contacting an outer surface of the receptacle 17. The annular lip 30 and the inner surface of the body portion 10 near the second end 20 of the body portion 10 are shaped to form a smooth, curved surface which mates with the outer surface of the receptacle 17 thereby decreasing frictional forces which tend to inhibit rotation of the receptacle 17.

An insert 32, in the form of a rubber tube, is provided for maintaining the probe 18 within the longitudinal passage 19 of the receptacle 17. The insert 32 has an outer diameter which is sized to fit snugly within the longitudinal passage 19 and an inner diameter selected to fit securely around an outer surface of the probe 18. An assortment of inserts 32, having different thicknesses, can be provided so that an appropriate insert 32 can be selected to match the dimensions of the particular probe 18 being used for a given application. An annular lip 34 along an outer surface of the insert 32 is provided as a stop surface to help maintain the insert 32 in position within the longitudinal passage 19 of the receptacle 17.

The probe holder 9 is designed to be used with any of a variety of conventional ultrasonic probes. For example, the probe holder 9 may be used with either a Doppler probe or a cardiac probe. Although the sizes and weights of conventional Doppler and cardiac probes vary considerably, the probe holder 9 of the present invention is sufficiently adaptable to accommodate a wide range of sizes and weights.

A locking cap 36 is positioned over the second end 20 of the body portion 10 for maintaining the receptacle 17 in a selected orientation within the body portion 10. The locking cap 36 comprises a generally tubular section which fits over the second end 20 of the body portion 10. The inner diameter of the tubular section is sized to fit over the second end 20 of the body portion 10 so that the locking cap 36 is maintained about the second end 20 of the body portion 10 by friction. Alternatively, the locking cap 36 may comprise internal threads which mate with external threads along the second end 20 of the body portion 10 for maintaining the locking cap 36 about the second end 20 of the body portion 10. An annular lip 37, formed along an interior surface of the tubular section of the locking cap 36, is provided as a stop surface to maintain the locking cap 36 about the second end 20 of the body portion 10. The locking cap 36 is moveable between a first position wherein the receptacle 17 is rotatable within the body portion 10 and a second position wherein the receptacle 17 is locked in a selected orientation.

A pressing ring 38 is positioned between the locking cap 36 and the outer surface of the receptacle 17 and an insert 39 is positioned between the pressing ring 38 and the outer surface of the receptacle 17. When the locking cap 36 is moved to lock the receptacle 17 in a selected position, the locking cap 36 exerts pressure on the insert 39 through the pressing ring 38. The insert 39 then contacts the outer surface of the receptacle 17 thereby using frictional force to hinder rotational movement of the receptacle 17.

Referring again to FIG. 1, it will be seen that the membrane 15, the membrane holder 12, the body portion 10, the receptacle 17, and the probe 18 define a sealed chamber which is fluid tight. Accordingly, the contacting medium, such as water, oil, or a viscous fluid, can be introduced into the sealed chamber. The contacting medium facilitates continuous conductance of ultrasound to and from the patient even as the probe 18 is maneuvered to optimize the resulting ultrasound images. The use of a contacting medium is especially important when the probe holder 9 is used in conjunction with a cardiac probe. Cardiac probes have flat scan heads which must continuously conduct ultrasound signals to and from the patient to produce a total visual image of the heart for analysis. Without the use of a contacting medium, rotation of the probe would cause the scan head to lose contact with the skin of the patient thereby resulting in non-conformed images.

Since the contacting medium functions to conduct ultrasound from the probe 18 to the patient, the contacting medium should provide the lowest possible acoustic attenuation at the working frequency of the transducer. Additionally, in order to minimize losses in ultrasound energy due to reflection, the acoustic impedance (i.e., the product of the sound speed and the density of the physical medium) should match the acoustic impedance of the biotissue in the place of contact between the probe 18 and the patient. The impedance value for soft human biotissue is typically about $1.4 \times 10^6$ to $1.7 \times 10^6$ kg/(m$^2$·sec). Therefore, distilled water (acoustic impedance=$1.5 \times 10^6$ kg/(m$^2$·sec)), normal saline, or any other fluid with an acoustic impedance greater than or equal to that of distilled water will be acceptable as a contacting medium.

Figure 3:
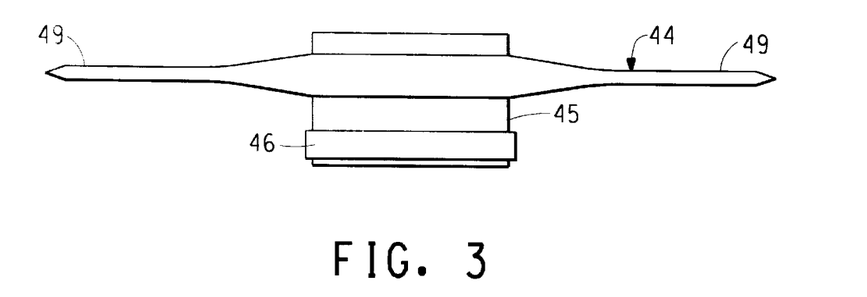
FIG. 3 is a side elevational view of a belt for securing the probe holder of FIG. 1 to a patient.

The probe holder 9 is secured to the patient using a belt 44 as depicted in FIG. 3. The belt 44 comprises a coupler 45 for releasably attaching the probe holder 9 to the belt 44. The coupler 45 comprises a tubular section having an inner diameter which enables the membrane holder 12 of the probe holder 9 to fit within the lumen of the tubular section of the coupler 45. A first side of a fastener 46, such as the male side of a hook-and-loop type fastener, is attached along an outer surface of the coupler 45. The first side of the fastener 46 is positioned along the coupler 45 to enable the first side of the fastener 46 to mate with a second side of the fastener 47, such as the female side of a hook-and-loop type fastener, which extends from the probe holder 9 in the form of straps 48. Accordingly, when the probe holder 9 is fitted within the coupler 45, the first and second sides of the fastener, 46 and 47 respectively, are connected to securely hold the probe holder 9 within the coupler 45. The belt 44 is secured to the patient by straps 49 in a conventional manner. The straps 48 may be configured as a harness or holster for securely fastening about the patient's chest, shoulders, or both chest and shoulders.

Figure 4:
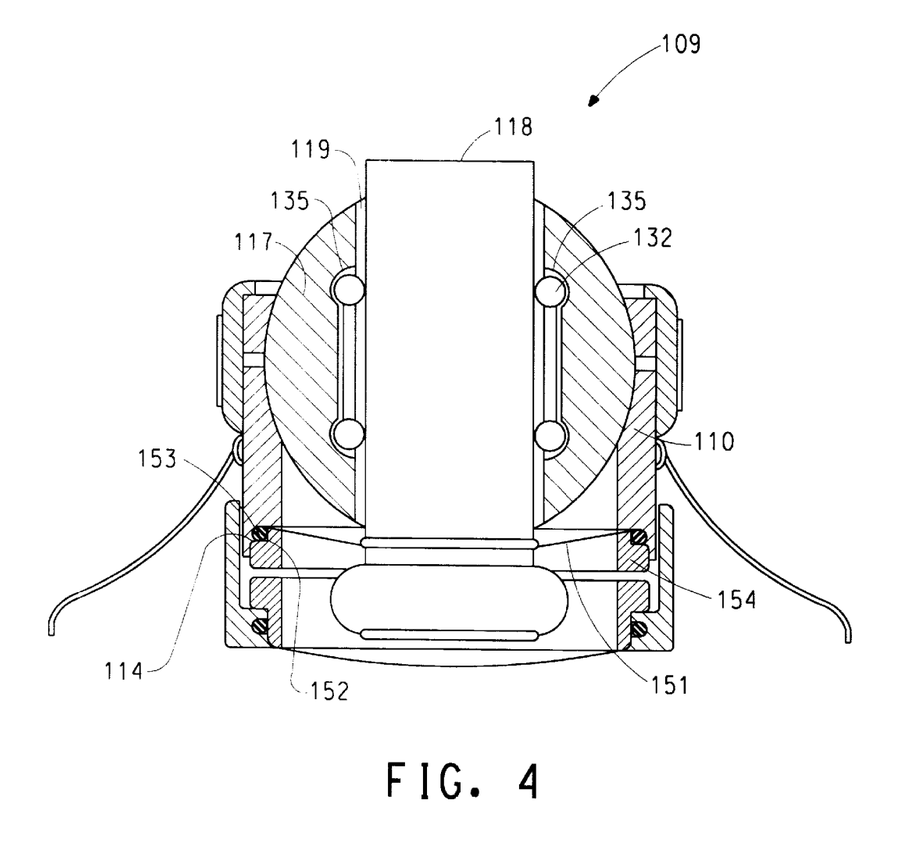
FIG. 4 is a partial cross-sectional view of an alternate embodiment of the probe holder in accordance with the present invention.

An alternate embodiment of the probe holder in accordance with the present invention is depicted in FIG. 4. The probe holder 109 of FIG. 4 is in many aspects similar to the probe holder 9 shown in FIGS. 1 and 2. However, the insert 32 of probe holder 9 is replaced by a locking cuff 132. The locking cuff is positioned within the channel 119 of receptacle 117. When the probe 118 is positioned within the channel 119, the locking cuff 132 pushes against the housing of the probe 118 to maintain the probe 118 within the channel 119. Toward that end, the locking cuff 132 is preferably inflatable. Accordingly, the probe 118 can be easily inserted within the channel 119 while the locking cuff 132 is deflated and then secured in place by inflating the cuff 132. One or more annular grooves 135 are formed along an interior surface of the channel 119. When the cuff 132 is inflated, portions of the cuff 132 expand into the grooves 135 thereby preventing the cuff 132 and probe 118 from shifting within the channel 119.

In addition, the probe holder 109 comprises a separating membrane 151 which is sealed about the housing of the probe 118 to provide a sealed chamber for containing the contacting medium which is isolated from the receptacle 117. An annular groove 152 is formed near the first end 114 of the body portion 110. The groove 152 is designed to accept a resilient O-ring 153. Accordingly, a periphery of the separating membrane 151 can be secured to the body portion 110 by positioning the O-ring 153 within the annular groove 152 so as to maintain the periphery of the separating membrane 151 within the groove 152. A separating membrane fixture 154, essentially identical to the membrane holder 25, is used to assist in securing the separating membrane 151 to the body portion 110.

When positioned within the receptacle 117, the probe 118 extends through an opening in the separating membrane 151. To provide a fluid tight seal between the separating membrane 151 and the housing of the probe 118, a membrane retaining ring 155 is used. The membrane retaining ring 155 is comprised of a stretchable rubber material which enables the retaining ring 155 to be stretched around the housing of the probe 118 to thereby seal a periphery of the opening in the separating membrane 151 to the probe 118.

Figure 5:
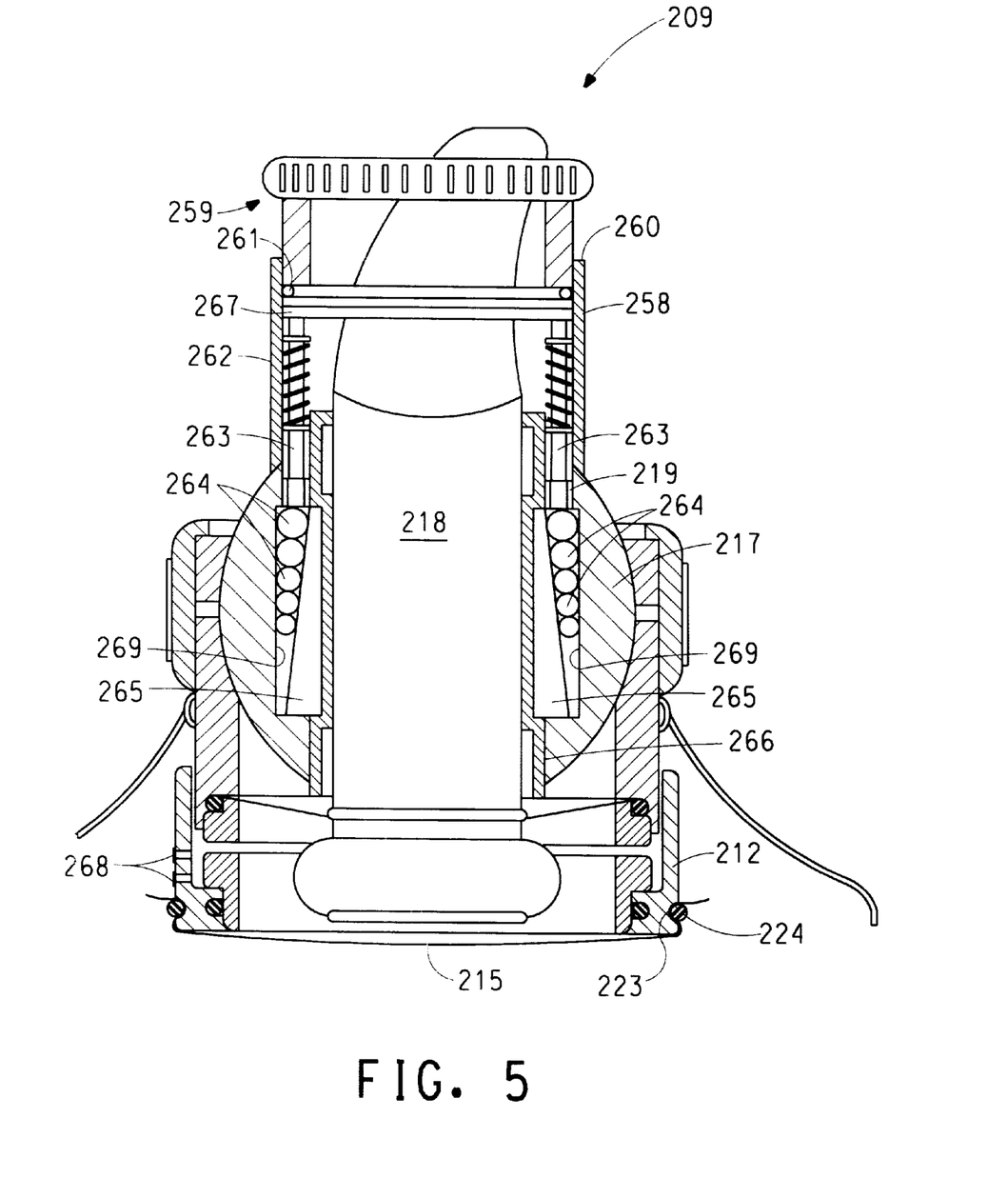
FIG. 5 is a partial cross-sectional view of another alternate embodiment of the probe holder in accordance with the present invention.

Another alternate embodiment of the probe holder in accordance with the present invention is depicted in FIG. 5. The probe holder 209 of FIG. 5 is in many aspects identical to the probe holder 109 depicted in FIG. 4. However, the probe holder 209 utilizes a multipodal locking mechanism configured to accommodate an even wider variety of probe structures than the probe holders 9 and 109. Toward that end, the receptacle 217 defines two longitudinal channels 269 formed along the interior of the channel 219 of the receptacle 217. A locking piece 265 is positioned within each of the longitudinal channels 269. Each locking piece 265 has a trapezoidal cross-section along its long axis which forms a narrow end and a wide end. The locking pieces 265 are placed within the channels 269 with the narrow ends of the locking pieces 265 in an upward direction. Accordingly, spaces are provided between the receptacle 217 and the locking pieces 265 wherein the spaces gradually narrow toward the bottom of the receptacle 217. Pressure equalizing balls 264 of various size are positioned within the spaces with the balls 264 arranged in order of increasing diameter toward the top of the receptacle 217. A generally cylindrical locking tube 266 is positioned within the longitudinal channel 219 of the receptacle 217 thereby maintaining the pressure equalizing balls 264 and the locking pieces 265 within the channels 269.

The probe holder 209 further comprises a cylindrical section 258 which extends from the receptacle 217 concentric with the channel 219 through the receptacle 217. The cylindrical section 258 may be attached to the receptacle 217 by tabs which extend from the cylindrical section 258 and mate with matching slots formed in the receptacle 217. A turning cylindrical cap or pusher 259 is positioned within a first end 260 of the cylindrical section 258. When the cap or pusher 259 is turned downward, a pushing ring 261 applies a downward force on a pushing piece 267. Two diametrically opposed pins 263 extend, from the pushing piece 267, longitudinally into the lumen of the cylindrical section 258. When the pushing piece is moved downwardly, the pins 263 are moved to extend into channels 269 of the receptacle 217 through holes in the receptacle 217, thereby contacting the pressure equalizing balls 264. Springs 262 are positioned over the pins 263.

The probe 218 is secured within the receptacle 217 by first positioning the probe 218 within the locking tube 266. The cylindrical cap 259 is then moved in a downward direction to cause the pushing ring 261 to exert a downward force on the pushing piece 267. The pins 263 in turn apply a force on the pressure equalizing balls 264 which move the rubber locking piece 265 and locking tube 266 to contact the probe 218. To remove the probe 218 from the probe holder 209, the cap 259 is turned and moved in an upward direction thereby releasing the pressure equalizing balls 264 and causing the locking piece 265 and locking tube 266 to disengage from the probe 218. Springs 262 provide a biasing force on the cap 259 to facilitate upward movement of the cap 259.

Additionally, the probe holder 209 differs from the probe holder 109 in that the membrane 215 is connected to the membrane holder 212 on an outer surface of the membrane holder 212. Specifically, the annular groove 223, which accepts O-ring 224, is formed around the outer surface of the membrane holder 212. With the arrangement depicted in FIG. 5, the O-ring 224 is easily accessible for removal from the groove 223 when a new membrane 215 is desired.

The probe holder 209 is also provided with injection holes 268. The injection holes 268 extend through the membrane holder 212 into the sealed chamber. Accordingly, the contacting medium can be injected directly into the sealed chamber through the injection holes 268.

Figure 6:
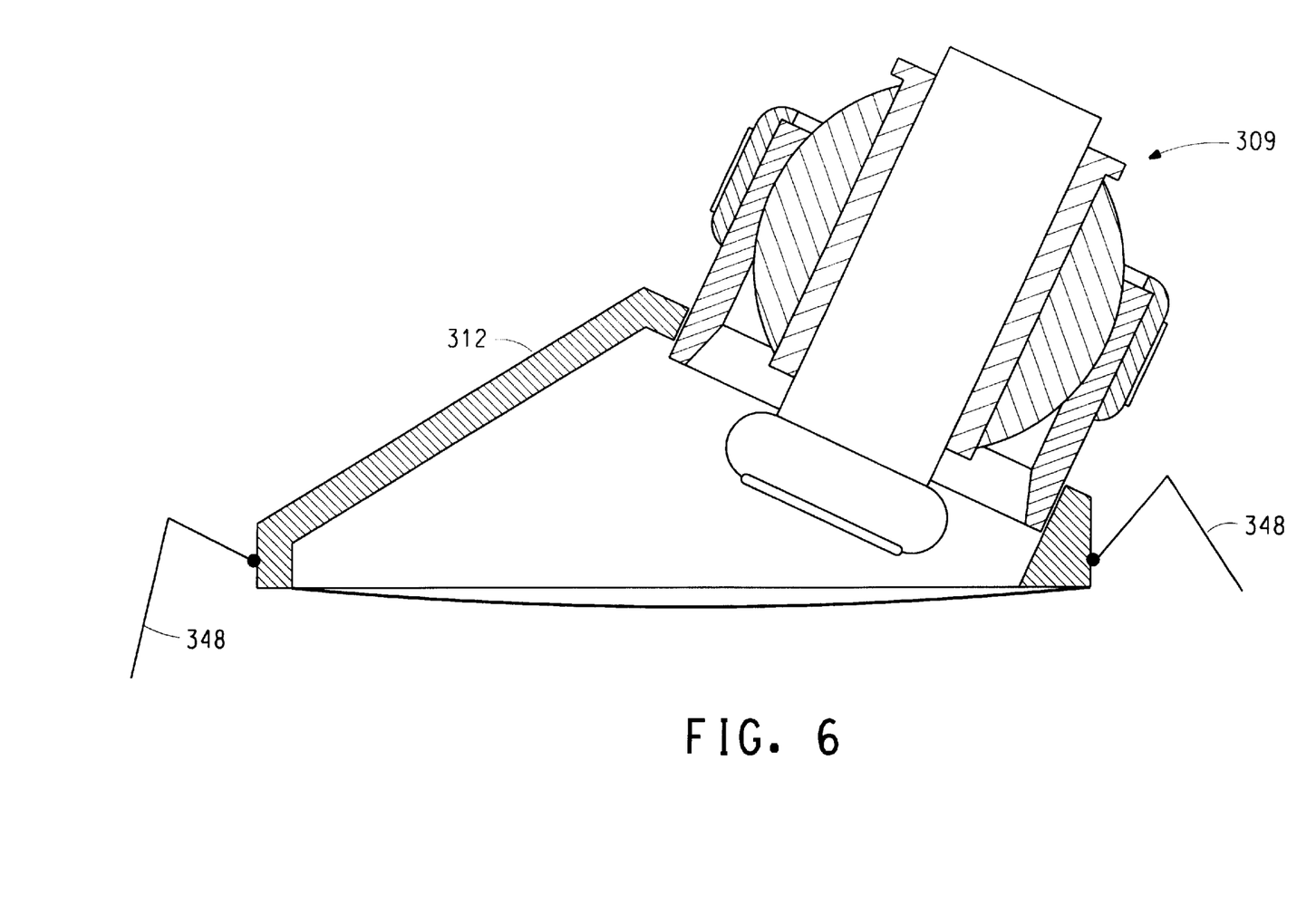
FIG. 6 is a partial cross-sectional view of yet another alternate embodiment of the probe holder in accordance with the present invention.

Yet another alternate embodiment of the probe holder in accordance with the present invention is depicted in FIG. 6. The probe holder 309 is essentially identical to the probe holder 9 of FIG. 1, except that the size and shape of the membrane holder 312 has been altered. Specifically, the membrane holder 312 has been elongated and angled to allow the probe holder 309 to be used to obtain subcostal images. In addition, the membrane holder 312 allows the probe holder 309 to cover more surface area of the patient without moving or readjusting the probe straps 348. Further, as described with reference to the embodiment of FIG. 5, the membrane 315 is attached to an outer surface of the membrane holder 312 to facilitate replacement of the membrane 315.

In operation, the apparatus of the present invention is used to produce ultrasonic images of a selected object. Toward that end, the probe is first positioned within the probe holder. When the probe holder depicted in FIGS. 1 or 6 is used, the probe is inserted within the rubber tube and the rubber tube and probe are positioned within the longitudinal passage of the receptacle.

When the apparatus depicted in FIGS. 4 or 5 is used, the separating membrane is first secured to the body portion. The probe is then inserted through the membrane retaining ring to maintain the separating membrane about the probe. The probe is then inserted within the longitudinal passage of the receptacle. With the probe positioned within the passage, the cuff or pusher is actuated to secure the probe within the receptacle.

The membrane is then secured to the membrane holder as described above. With the membrane secured to the membrane holder, a quantity of a contacting medium is then placed within the membrane holder. The quantity of fluid should be sufficient to substantially completely engulf the head of the probe when the apparatus is used to acquire images. The membrane holder is then attached to the body portion of the probe holder. Care must be taken to insure that the fluid is substantially maintained within the sealed chamber of the apparatus.

Alternatively, when the membrane holder is equipped with injection holes, the membrane holder can be first attached to the body portion of the probe holder. The contacting medium is then injected through the injection holes into the sealed chamber.

The probe holder is then attached to the patient. When the belt depicted in FIG. 3 is used, the coupler is positioned against the patient with the lumen of the coupler adjacent to the object of interest. The straps are then secured to the patient to maintain the coupler in the desired position.

The probe holder is then positioned within the coupler with the membrane in contact with the patient's skin. The ends of the fastener are connected to secure the probe holder within the coupler. If desired, an ultrasonic gel can be applied on the surface of the membrane which is in contact with the patient.

The orientation of the probe is then adjusted by rotating the probe and the receptacle within the body portion. To insure optimal placement of the probe holder with respect to the object of interest, images from the probe can be monitored as the orientation of the probe is changed. When the image of the object of interest is optimized, the probe is secured in that orientation by activating the locking cap.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for holding a probe comprising:
   a. a body portion having a longitudinal bore;
   b. a membrane holder, defining an opening, positioned over a first end of the body portion;
   c. a membrane positioned to cover the opening of the membrane holder; and
   d. a receptacle for receiving the probe, the receptacle having a longitudinal passage and rotatably positioned within the longitudinal bore of the body portion at a second end of the body portion,
   wherein the membrane, the membrane holder, the body portion, the receptacle, and the probe define a sealed chamber.

2. The apparatus of claim 1 comprising locking means operatively connected to the body portion for maintaining the receptacle in a selected orientation.

3. The apparatus of claim 2 wherein the locking means comprises:
   a. a locking cap positioned over the second end of the body portion;
   b. a pressing ring positioned between the locking cap and an outer surface of the receptacle; and
   c. an insert positioned between the pressing ring and the outer surface of the receptacle.

4. The apparatus of claim 3 wherein the locking cap is movable between a first position wherein the receptacle is rotatable within the body portion and a second position wherein the locking cap exerts pressure on the insert through the pressing ring to maintain the receptacle in a selected orientation.

5. The apparatus of claim 1 wherein the membrane holder comprises a longitudinal groove and a ring positioned within the longitudinal groove for holding the membrane to cover the opening.

6. The apparatus of claim 5 wherein the membrane holder comprises a membrane fixture positioned within the opening of the membrane holder for securing the membrane to the membrane holder.

7. The apparatus of claim 1 wherein the receptacle comprises a probe securing means positioned within the longitudinal passage of the receptacle for retaining the probe within the receptacle with a window of the probe directed generally toward the opening in the membrane holder.

8. The apparatus of claim 7 wherein the probe securing means comprises a rubber tube.

9. The apparatus of claim 7 wherein the probe securing means comprises a locking cuff.

10. The apparatus of claim 9 wherein the locking cuff comprises an inflatable locking cuff.

11. The apparatus of claim 7 wherein the probe securing means comprises a multipodal locking device.

12. The apparatus of claim 1 comprising an annular lip concentric with the longitudinal bore of the body portion formed along an inner surface of the body portion for contacting an outer surface of the receptacle.

13. The apparatus of claim 1 comprising means for securing the apparatus to a subject.

14. The apparatus of claim 13 wherein the securing means comprises:
   a. a belt securable to a subject; and
   b. coupling means for securing the body portion to the belt with the membrane in contact with the subject.

15. An apparatus for holding a probe comprising:
   a. a body portion having a longitudinal bore;
   b. a lower membrane holder, defining an opening, positioned over a first end of the body portion;
   c. a lower membrane positioned to cover the opening of the membrane holder;
   d. a receptacle for receiving the probe, the receptacle having a longitudinal passage and rotatably positioned within the longitudinal bore of the body portion at a second end of the body portion;
   e. an upper membrane having an opening, the upper membrane positioned over the longitudinal bore of the body portion at the first end of the body portion; and
   f. a sealing member for securing a perimeter of the opening in the upper membrane to an outer surface of the probe,
   wherein the lower membrane, the lower membrane holder, the body portion, the upper membrane, and the probe define a sealed chamber.

16. The apparatus of claim 15 comprising locking means operatively connected to the body portion for maintaining the receptacle in a selected orientation.

17. The apparatus of claim 16 wherein the locking means comprises:
   a. a locking cap positioned over the second end of the body portion;
   b. a pressing ring positioned between the locking cap and an outer surface of the receptacle; and
   c. an insert positioned between the pressing ring and the outer surface of the receptacle.

18. The apparatus of claim 17 wherein the locking cap is movable between a first position wherein the receptacle is rotatable within the body portion and a second position wherein the locking cap exerts pressure on the insert through the pressing ring to maintain the receptacle in a selected orientation.

19. The apparatus of claim 15 wherein the lower membrane holder comprises a lower membrane fixture positioned within the opening of the lower membrane holder for securing the lower membrane to the lower membrane holder and the body portion comprises an upper membrane fixture positioned within the longitudinal bore of the body portion at the first end of the body portion for securing the upper membrane to the body portion.

20. The apparatus of claim 19 wherein the lower membrane holder comprises a longitudinal groove and a ring positioned within the longitudinal groove for holding the lower membrane to cover the opening.

21. The apparatus of claim 15 comprising a probe securing means positioned within the longitudinal passage of the receptacle for retaining the probe within the receptacle with a window of the probe directed generally toward the opening in the lower membrane holder.

22. The apparatus of claim 21 wherein the probe securing means comprises a rubber tube.

23. The apparatus of claim 21 wherein the probe securing means comprises a locking cuff.

24. The apparatus of claim 23 wherein the locking cuff comprises an inflatable locking cuff.

25. The apparatus of claim 21 wherein the probe securing means comprises a multipodal locking device.

26. The apparatus of claim 15 comprising an annular lip concentric with the longitudinal bore of the body portion formed along an inner surface of the body portion for contacting an outer surface of the receptacle.

27. The apparatus of claim 15 comprising means for securing the apparatus to a subject.

28. The apparatus of claim 27 wherein the securing means comprises:
   a. a belt securable to a subject; and
   b. coupling means for securing the body portion to the belt with the lower membrane in contact with the subject.

29. A method for holding a probe adjacent to a subject comprising the steps of:
   a. positioning the probe within a probe holder, the probe holder comprising:
      i. a body portion having a longitudinal bore;
      ii. a membrane holder, defining an opening, positioned over a first end of the body portion;
      iii. a membrane positioned to cover the opening of the membrane holder; and
      iv. a receptacle for receiving the probe, the receptacle having a longitudinal passage and rotatably positioned within the longitudinal bore of the body portion at a second end of the body portion,
   wherein the membrane, the membrane holder, the body portion, the receptacle, and the probe define a sealed chamber;
   b. inserting a contacting medium within the sealed chamber of the probe holder; and
   c. securing the probe and probe holder to the subject.

30. A method for holding a probe adjacent to a subject comprising the steps of:
   a. positioning the probe within a probe holder, the probe holder comprising:
      i. a body portion having a longitudinal bore;
      ii. a lower membrane holder, defining an opening, positioned over a first end of the body portion;
      iii. a lower membrane positioned to cover the opening of the membrane holder;
      iv. a receptacle for receiving the probe, the receptacle having a longitudinal passage and rotatably positioned within the longitudinal bore of the body portion at a second end of the body portion;
      v. an upper membrane having an opening, the upper membrane positioned over the longitudinal bore of the body portion at the first end of the body portion; and
      vi. a sealing member for securing a perimeter of the opening in the upper membrane to an outer surface of the probe,
   wherein the lower membrane, the lower membrane holder, the body portion, the upper membrane, and the probe define a sealed chamber;
   b. inserting a contacting medium within the sealed chamber of the probe holder; and
   c. securing the probe and probe holder to the subject.

* * * * *